(12) United States Patent  
Schmidt (10) Patent No.: US 6,561,967 B2
(45) Date of Patent: May 13, 2003

(54) INTERSTITIAL BRACHYTHERAPY DEVICE AND METHOD

(76) Inventor: Bruno Schmidt, 5836 Portsmouth Dr., Tampa, FL (US) 33615

( * ) Notice: Subject to any disclaimer, the term of this patent is extended or adjusted under 35 U.S.C. 154(b) by 0 days.

(21) Appl. No.: 09/829,190

(22) Filed: Apr. 9, 2001

(65) Prior Publication Data

US 2002/0013509 A1 Jan. 31, 2002

Related U.S. Application Data

(63) Continuation-in-part of application No. 08/989,727, filed on Dec. 12, 1997, now Pat. No. 6,213,932.

(51) Int. Cl.[7] .............................................. A61M 36/12
(52) U.S. Cl. ......................................................... 600/7
(58) Field of Search ........................... 600/1–8; 604/57, 604/59–64, 93.01; 221/22, 23, 67, 155; 227/176.1, 177.1; 250/507.1; 976/DIG. 350

(56) References Cited

U.S. PATENT DOCUMENTS

| | | | | |
|---|---|---|---|---|
| 2,620,796 A | * | 12/1952 | Eriksen et al. ................. 221/18 |
| 4,451,254 A | * | 5/1984 | Dinius et al. ................ 206/535 |
| 5,522,797 A | * | 6/1996 | Grimm ........................ 604/61 |
| 5,860,909 A | * | 1/1999 | Mick et al. ..................... 600/7 |
| 6,007,474 A | * | 12/1999 | Rydell ............................ 600/7 |
| 6,102,844 A | * | 8/2000 | Ravins et al. ................... 600/7 |
| 6,358,195 B1 | * | 3/2002 | Green et al. .................... 600/7 |

OTHER PUBLICATIONS

Author: Mick Radio–Nuclear Instruments, Inc. brochure entitled "Mick 200–TP applicator package".

* cited by examiner

Primary Examiner—Max F. Hindenburg
Assistant Examiner—Joseph A. Cadugan
(74) Attorney, Agent, or Firm—Stanley M. Miller (57) ABSTRACT

An interstitial brachytherapy device includes an applicator having an elongate barrel and a plurality of radioactive seed-containing cartridges releasably connected to the elongate barrel along its longitudinal extent. Each cartridge includes a handle, a hollow housing within which is stacked the seeds, and a neck formed integrally with the handle. The neck is slideably received within the hollow housing and its free end abuts the top of the stack of seeds. A plurality of seed-discharging chambers is formed in the elongate barrel at longitudinally spaced intervals along the extent of the elongate barrel and each chamber is in alignment with each cartridge. The seeds in each hollow housing are urged toward their associated seed-discharging chamber by a bias member having a leading end connected to the hollow housing and a trailing end connected to the handle.

17 Claims, 6 Drawing Sheets

INTERSTITIAL BRACHYTHERAPY DEVICE AND METHOD

This application is a continuation-in-part of Ser. No. 08/989,727 filed Dec. 12, 1997 now U.S. Pat. No. 6,213,932.

BACKGROUND OF THE INVENTION

1. Field of the Invention

This invention relates, generally, to surgical tools. More particularly, it relates to an apparatus that implants radioactive seeds into a prostate gland or other internal organ.

2. Description of the Prior Art

U.S. Pat. No. 6,213,932 to the present inventor includes a description of the prior art in this field up to the time of its filing. That patent is hereby incorporated into this disclosure by reference.

The invention disclosed in that patent application is the most relevant prior art to the present disclosure. That invention includes an elongate barrel having a radially extending opening formed therein for reception of a cartridge that holds a plurality of radioactive seeds for implanting in a cancerous gland or organ. The cartridge includes a loop-shaped bias means having a first end formed integrally with the cartridge and a second end that is slideably received within the cartridge. The second end bears against the seeds stacked in the cartridge and thus urges the lowermost seed in the cartridge to enter a seed discharge chamber within the elongate barrel. A plunger rod is introduced into an open trailing end of the elongate barrel and shoves a lowermost seed out of the seed discharge chamber into a needle, positioned at the leading end of the elongate barrel, that is inserted within the gland or organ to be treated. The needle can be retracted while the seed is held motionless by the plunger rod or the seed can be pushed out of the end of the needle. After a seed has been implanted by this method, the plunger rod is retracted to the trailing end of the elongate barrel so that the bias means may urge another seed from the lowermost end of the cartridge into the seed discharge chamber and the process is then repeated.

While this earlier device overcame the limitations of the prior art devices that were extant at the time of the invention of said earlier device, a very astute observer could find a limitation of that device. Specifically, the loop-shaped bias means lies in a plane that bisects the longitudinal axis of symmetry of the elongate barrel. Accordingly, the loop-shaped part thereof has a substantial longitudinal extent. Thus, only one of said bias means can be accommodated along the longitudinal extent of said elongate barrel. Although a cartridge might hold up to fifteen to sixteen seeds, it is not uncommon for a single procedure to require seventy to one hundred seeds. This means that the physician is required to introduce a new fully-loaded cartridge several times during the course of a procedure. These cartridges are usually kept in a shielded container apart from the applicator. To reload the applicator requires disengagement of the empty cartridge, retrieval of a full cartridge from a shielded container, and re-insertion of the full cartridge into the applicator. During this process, the physician's eyes and attention are taken away from the needle and the applicator. This awkward reloading process may result in jiggling of the instruments causing movement of the cutting edges of the needle tip within the prostate gland or other internal organ. Such movement is undesirable.

What is needed, then, is an improved design that substantially reduces the number of times a physician has to divert attention and re-load a new cartridge into the elongate barrel. More particularly, what is needed is: 1) a way to increase the seed-carrying capacity of the cartridge; 2) to increase the cartridge-carrying capacity of the applicator; and 3) better shielding of the radioactive seeds from physicians and operating room personnel.

However, in view of the prior art considered as a whole at the time the present invention was made, it was not obvious to those of ordinary skill in the pertinent art how the needs for enhanced seed and cartridge capacity and improved shielding could be fulfilled.

SUMMARY OF THE INVENTION

The longstanding but heretofore unfulfilled need for an interstitial brachytherapy device having an increased seed and cartridge capacity and improved shielding, thus making it easy and expedient for a physician to reload, is now met by a new, useful, and nonobvious invention. The novel interstitial brachytherapy device of this invention includes an applicator having a number of novel and advantageous features. The novel applicator is easily disassembled for cleaning, made of a clear plastic material that enables its internal operation to be viewed, and provides substantial radiation shielding of seeds held therewithin. The novel applicator has an elongate barrel of predetermined longitudinal extent. An elongate throughbore is formed in the elongate barrel in parallel relation to a longitudinal axis of symmetry thereof. A manually-operated, elongate plunger rod is slideably mounted in the elongate throughbore and a hollow needle is detachably secured to the elongate barrel at a leading end thereof. A clear plastic tube connects the seed discharge chamber of the cartridge to the lumen (internal diameter) of the needle. A plurality of slots is formed in the elongate barrel, said slots being longitudinally spaced apart from one another.

A plurality of cartridges is releasably coupled to the elongate barrel. Each of the cartridges has a leading end releasably engaged to an associated slot of the plurality of slots. Each cartridge includes a hollow housing adapted to hold a plurality of radioactive seeds in substantially vertically stacked relation to one another.

The novel structure further includes a handle having an elongate neck depending therefrom. The neck is adapted to be slideably received within the hollow housing and has a leading end adapted to abut an uppermost radioactive seed of said plurality of radioactive seeds. The handle and neck are made of an opaque radiation shielding material which shields the plurality of seeds in an upward direction. A bias means has a leading end engaged to the hollow housing and a trailing end engaged to the handle so that the bias means urges the neck to bear against the plurality of radioactive seeds and to drive them toward their associated seed discharge chamber.

In a preferred embodiment, the bias means is a pair of coil springs having respective trailing ends releasably secured to opposite sides of the handle and having respective leading ends releasably secured to opposite sides of the hollow housing.

In an alternative embodiment, the bias means is a pair of flexible and resilient plastic members of sinusoidal construction. Each of the plastic members has a first end integrally formed with the handle and a second end integrally formed with the hollow housing.

Each cartridge that forms a part of the novel interstitial brachytherepy device is provided in the form of a hollow housing having a generally parallelepiped construction.

Each hollow housing has a vertical extent substantially exceeding its respective width and depth extents and is adapted to receive a plurality of radioactive seeds that are vertically stacked therewithin.

The hollow housing may be made of transparent plastic so that the number of radioactive seeds within the housing is ascertainable upon visual inspection of the housing. Alternatively, the housing may be shielded against radiation and therefore be of opaque construction. Since the cartridge body is made in two parts (main housing and front cover), the main housing could be opaque offering protective shielding (along with the handle) on five of the six sides of the seeds in the hollow housing. The front cover could be clear, thereby enabling visual verification of the seeds, or it could also be opaque and shielded. Such an embodiment would provide a completely shielded cartridge heretofore unknown to the art.

When the housing is opaque, a plurality of vertically spaced apart symbols are provided along the extent of the neck so that when the neck is disposed within the hollow housing the number of visible symbols on the neck represents the number of radioactive seeds within the housing.

The novel method for implanting radioactive seeds in a prostate gland or other internal organ includes the steps of preloading a plurality of cartridges with a plurality of radioactive seeds, forming a seed discharge chamber in a preselected end of each of the cartridges, providing an elongate applicator having an elongate throughbore formed therein, mounting a hollow needle at a leading end of the applicator, forming a plurality of slots in the applicator along its longitudinal extent so that the slots are longitudinally spaced apart from one another, inserting a cartridge into each of the slots, thereby providing ease of reloading, and inserting a plunger rod into the elongate throughbore and driving a seed in the seed discharge chamber through a connecting tube affixed to the throughbore of the applicator and through the needle mounted to the nose of the applicator into the prostate gland or other internal organ.

As the cartridges are emptied, they can be easily removed and a full cartridge installed due to the close proximity of stored full cartridges within the applicator. This allows the physician to better maintain concentration on the surgical procedure. Every seed within the applicator is completely shielded by the applicator itself and the handle and neck of each cartridge, all of which may be made of a suitable shielding material. A completely shielded cartridge is also possible by making all components of the cartridge out of opaque shielding material. However, this sacrifices any visual verification of the seeds within the cartridge and the physician must rely on the indicator symbols provided on the neck of the handle.

It is therefore clear that increasing the seed capacity of an interstitial brachytherapy device is an important object of this invention.

A closely related object is to provide a new cartridge design that enables a plurality of cartridges to be mounted along the longitudinal extent of the elongate barrel of such a device.

Another object is to significantly reduce radiation exposure by providing the applicator and cartridge with substantial shielding capabilities.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
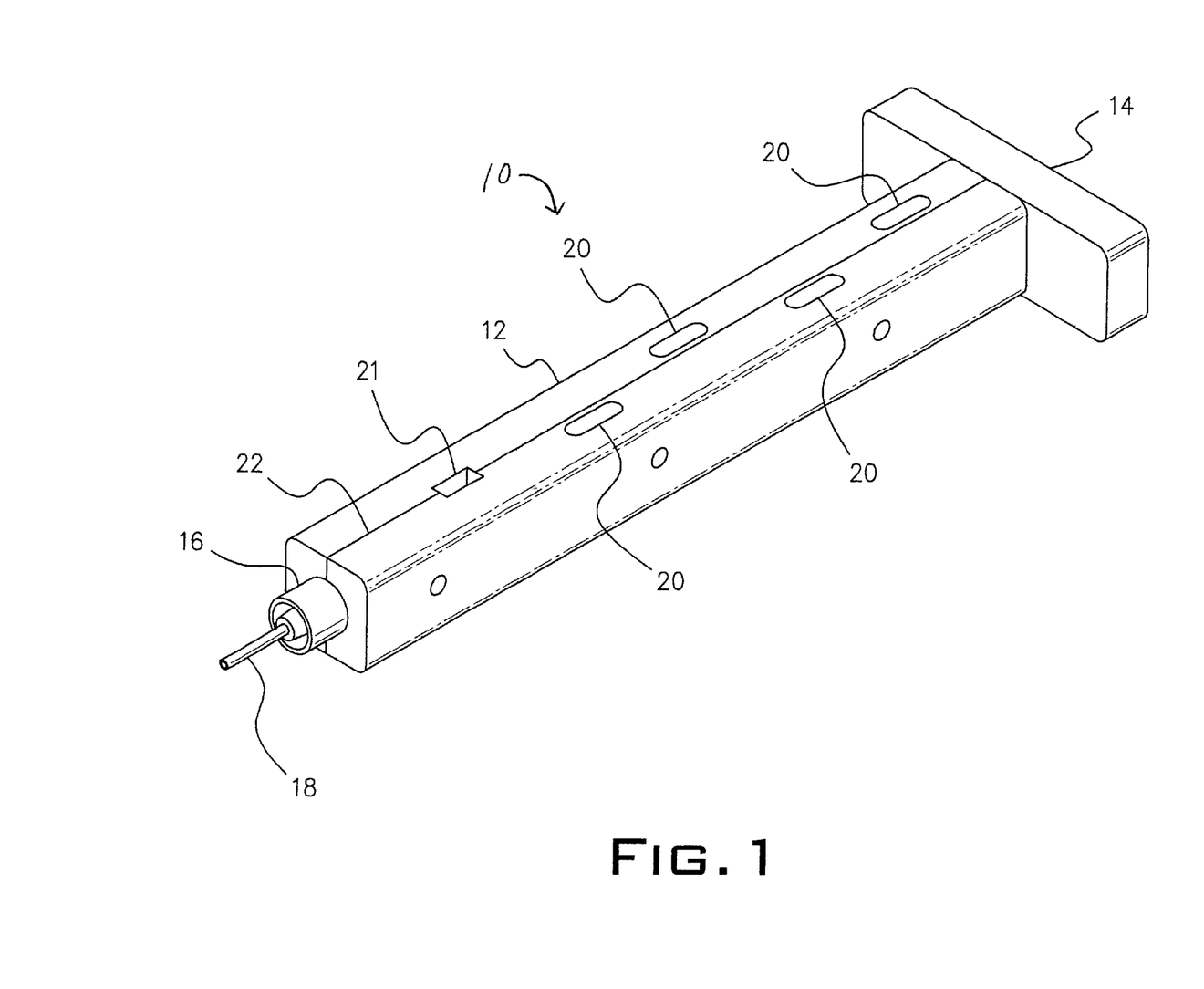
FIG. 1 is a perspective view of the elongate barrel of this invention.

Referring now to FIG. 1, it will there be seen that an exemplary embodiment of the seed applicator of this invention is denoted as a whole by the reference numeral 10.

Novel applicator 10 includes elongate barrel 12 and a flat handle 14 disposed transversely to the longitudinal axis of barrel 12 at the trailing end thereof. Adaptor member 16 which may be of the well-known luer lock type is mounted to the leading end of barrel 12 and can be attached to a standard needle luer lock hub. Connecting tube 18 protrudes from adaptor member 16 and in practice slides inside the needle lumen. Like its predecessor disclosed in the incorporated patent, the structure resembles a conventional syringe structure and thus its method of use is largely intuitive and non-intimidating for a physician used to handling syringes. However, elongate barrel 12 has a generally square cross-section, unlike the circular cross-section of a syringe barrel. This square shape provides enhanced gripping and manipulation.

In this particular embodiment, there are four slot-like openings used for shielded storage of loaded cartridges, collectively denoted 20, formed in elongate barrel 12, and one operational slot 21 that accommodates the cartridges and seeds therewithin to be dispensed. The invention is not limited to any particular number of slots. A longer barrel may accommodate more storage slots, for example. The slots are preferably equidistantly spaced apart from one another as depicted although such spacing is not critical. As will be understood as this description proceeds, each of these slots slidingly receives the radially innermost end of a seed cartridge that is not illustrated in FIG. 1. When fully seated, each cartridge is snap-fittingly secured into its associated slot.

Figure 2:
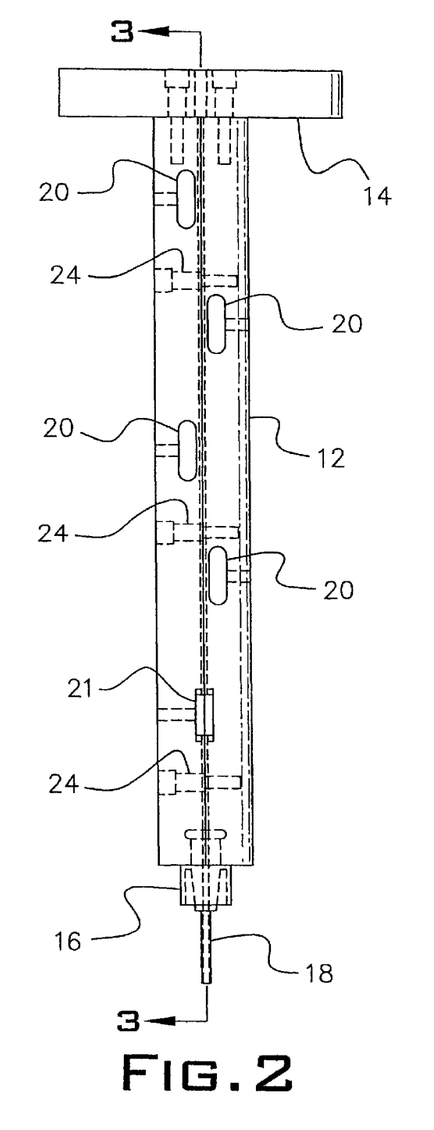
FIG. 2 is a side elevational view of said elongate barrel.
Figure 2A:
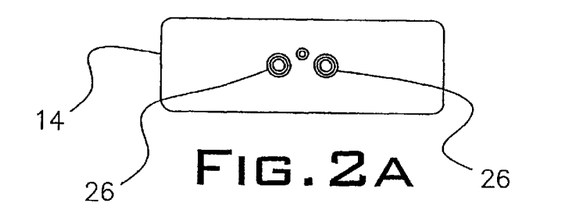
FIG. 2A is a top plan view thereof.

Barrel 12 is made in two halves as indicated by parting line 22. As indicated in FIG. 2, the two halves are joined to one another by countersunk screws, not shown, that are received within countersunk bores collectively denoted 24. As indicated in FIG. 2A, a pair of countersunk screws 26 join transversely disposed handle 14 to the trailing end of barrel 12.

Figure 3:
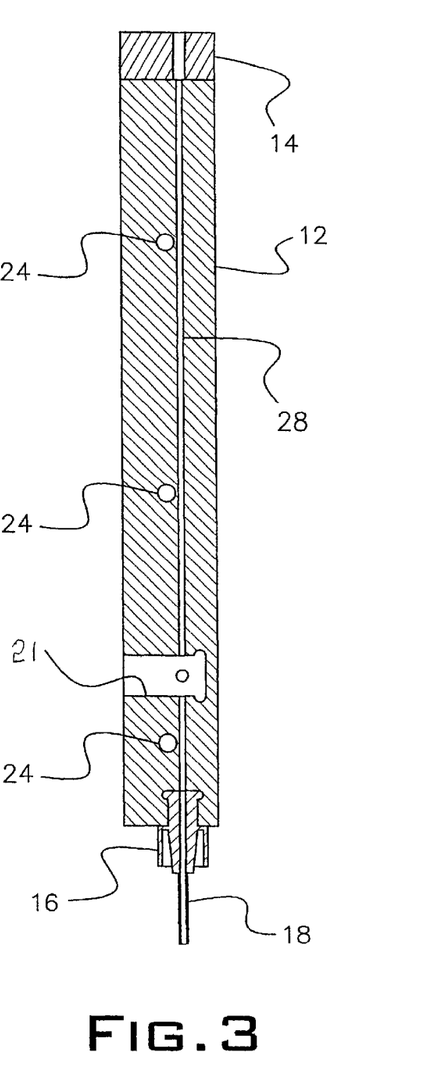
FIG. 3 is a sectional view taken along line 3—3 in FIG. 2.

FIG. 3 perhaps best depicts bore 28 that receives a plunger rod, not shown, used to push seeds from each seed discharge chamber 48 (FIGS. 4 and 5) from operational slot 21 into connecting tube 18. Connecting tube 18 extends from operational slot 21 through luer lock adaptor 16 and into the needle lumen, not shown.

Figure 4:
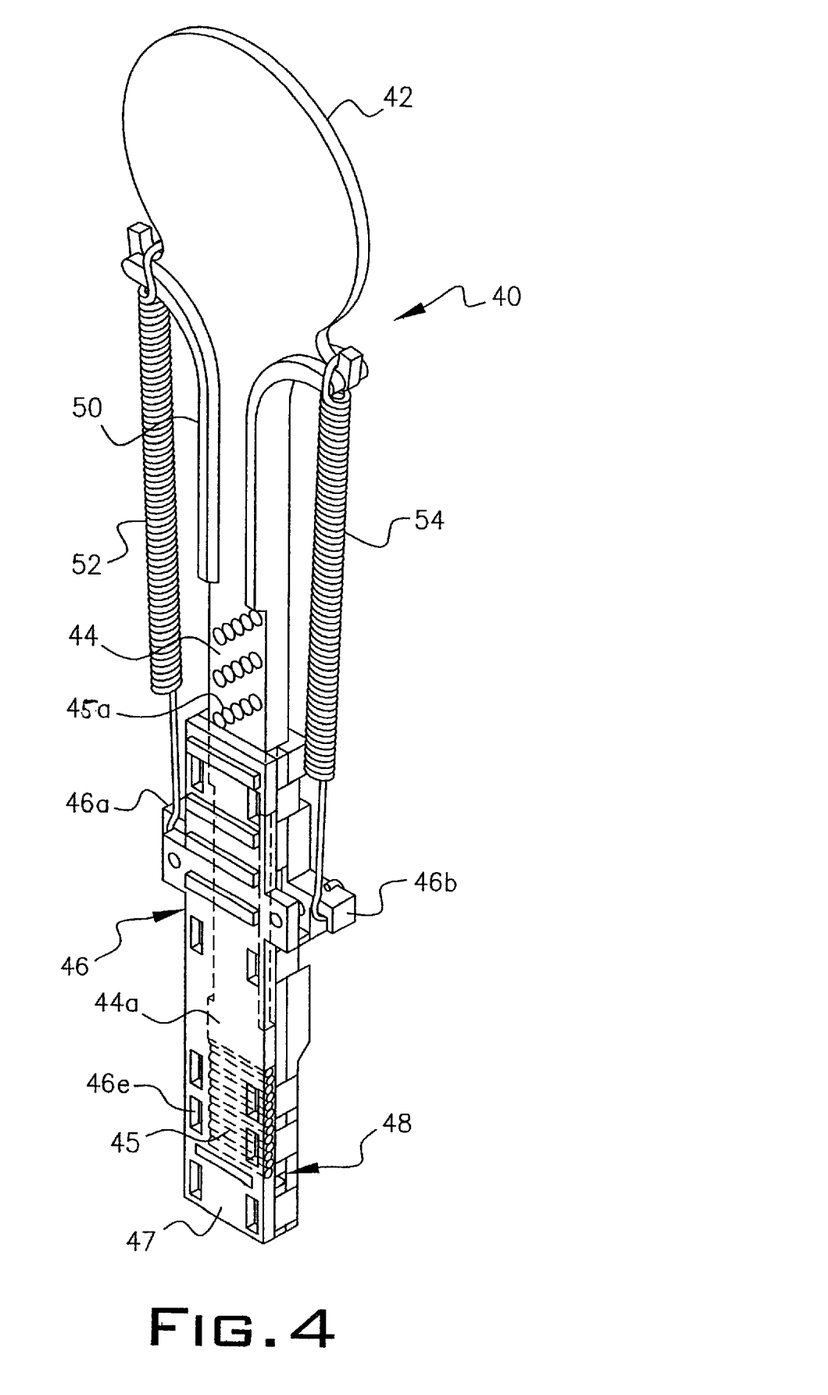
FIG. 4 is a perspective view of a first embodiment of the novel cartridge.
Figure 5:
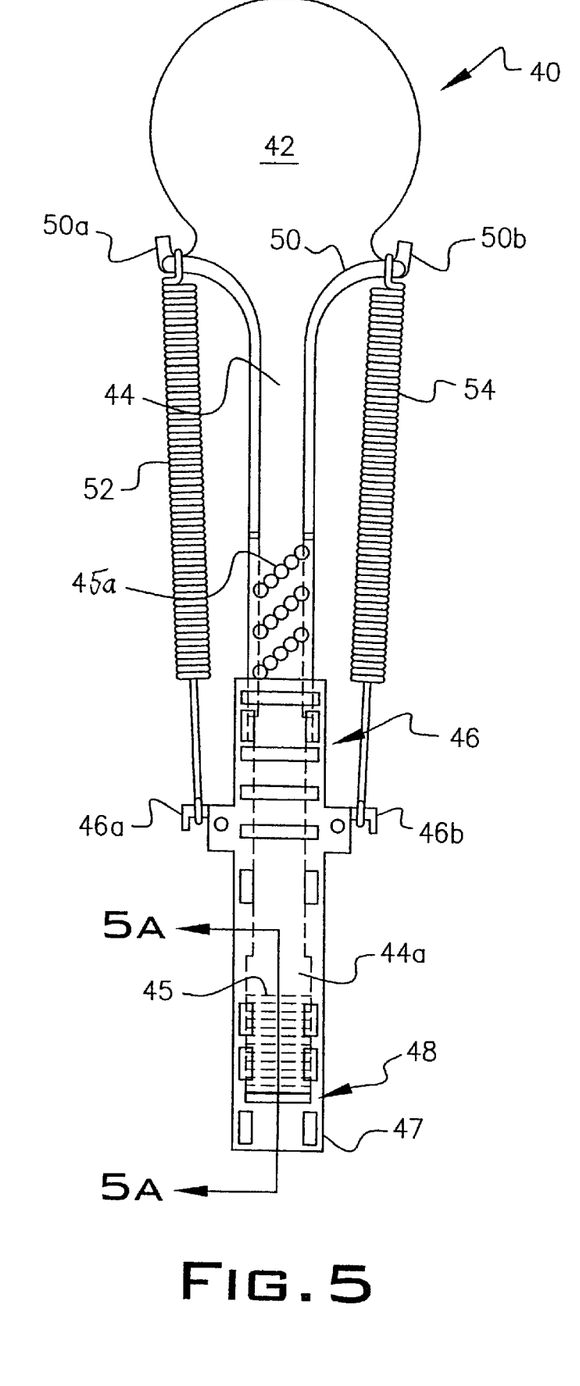
FIG. 5 is a front elevational view of said cartridge.

Each opening 20 and 21 has a generally rectangular cross-section and is adapted to receive the leading or radially innermost end of novel cartridge 40 (FIGS. 4 and 5). Cartridge 40 includes generally circular flat handle 42, which provides a mounting location for a label, having an elongate neck 44 integrally formed therewith and depending therefrom. The lowermost or radially innermost end 44a of neck 44 bears against seeds 45 disposed in hollow housing 46 of cartridge 40, as will become clear as this description proceeds, driving them toward their respective seed discharge chambers 48.

Frame 50 receives the lower end of handle 42 and neck 44 and also provides a releasable mounting means 50a, 50b for the respective trailing ends of stainless steel springs 52, 54. The respective leading ends of said springs are releasably secured to housing 46 at arms 46a, 46b thereof. Since the leading end 47 of housing 46 is received within its associated seed discharge chamber and snap-fittingly engaged thereto, housing 46 provides an immovable base. Accordingly, the tension in springs 52, 54 pulls neck 44 into the hollow interior of housing 46 and thus drives seeds 45 toward their associated seed discharge chamber 48. Each seed discharge chamber is the lowermost end of its associated cartridge. Springs 52, 54 are releasably mounted to facilitate loading of the cartridge if needed.

Figure 5A:
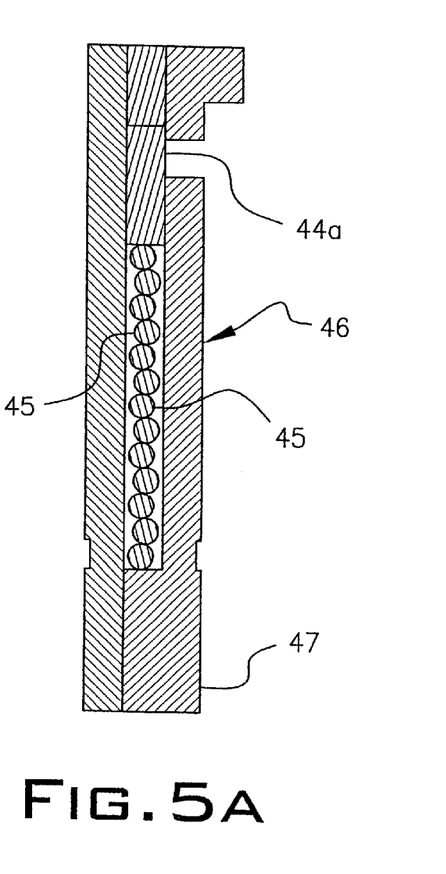
FIG. 5A is an enlarged sectional view taken along line 5A—5A in FIG. 5.

Sixteen seeds 45 (or sixteen seeds and a spacer used for shipping) can be stored within the hollow housing at the beginning of a procedure, as indicated in FIGS. 5 and 5A. Thus, when five cartridges 40 are inserted into their respective slots 20 and 21, a total of eighty seeds may be implanted in a gland or organ without awkward replacement of spent cartridges as previously mentioned or adding any additional cartridges or re-loading any cartridge. This advance is made possible in large part by the unique design of cartridges 40. Specifically, the longitudinal extent of base 42 is substantially less than the longitudinal extent of the loop-shaped means of the prior art, thereby enabling a plurality of said cartridges to be arrayed along the extent of elongate barrel 12 in closely spaced longitudinal relation to one another for ease of transfer into operational slot 21.

Figure 6:
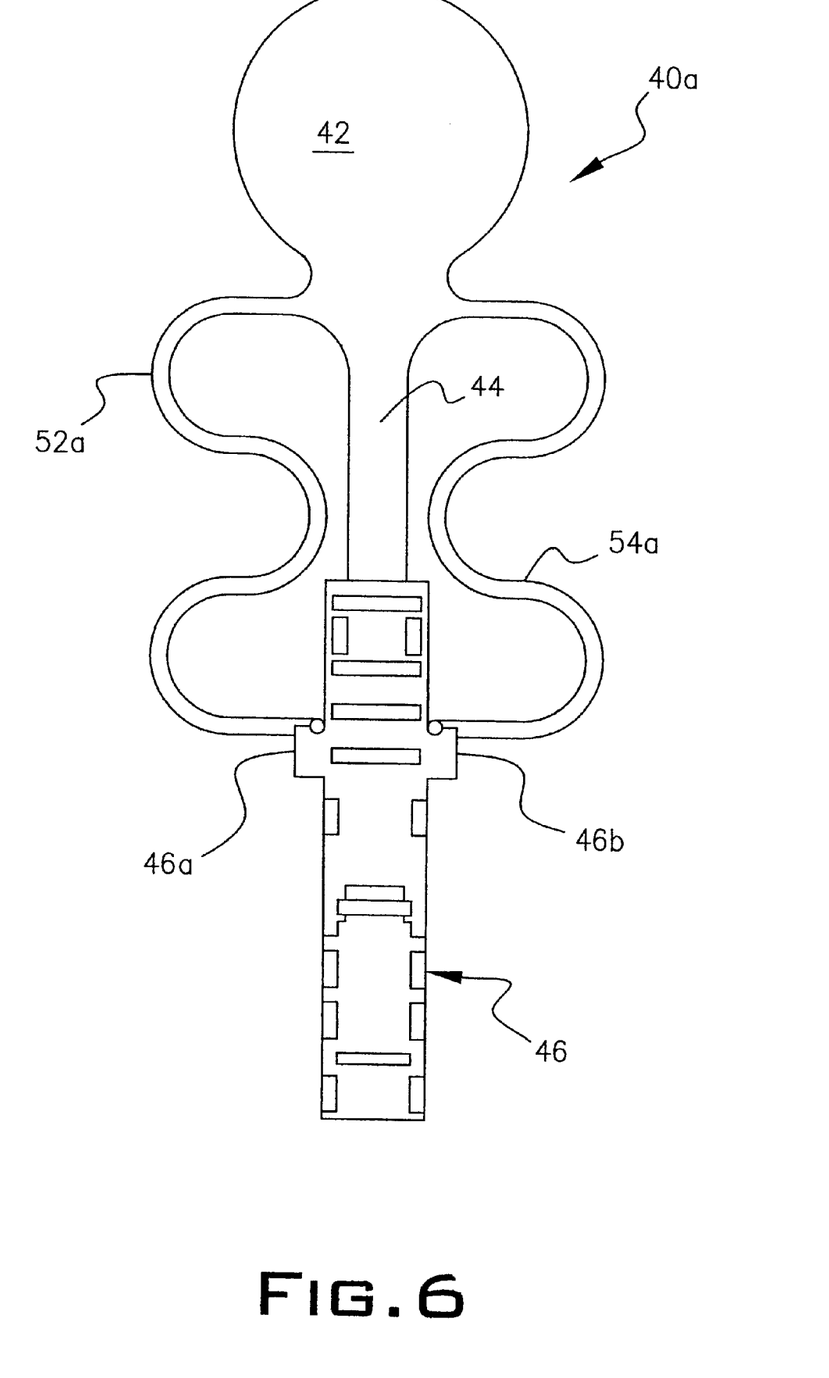
FIG. 6 is a front elevational view of an alternative embodiment of the novel cartridge.
Figure 7A:
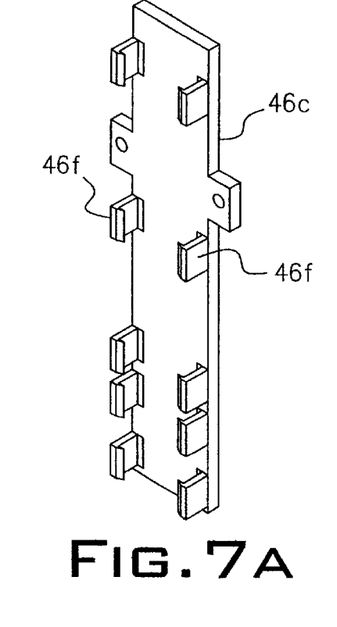
FIG. 7A is a perspective view of the inside of a front cover of the seed-containing housing of the novel cartridge.
Figure 7B:
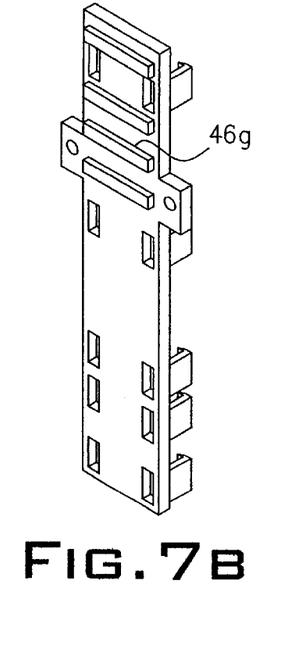
FIG. 7B is a perspective view of the outside of the front cover depicted in FIG. 7A.
Figure 8A:
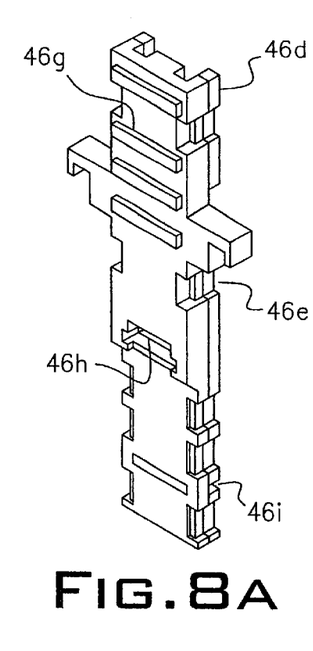
FIG. 8A is a perspective view of the outside of the back cover of the seed-containing housing of the novel cartridge.
Figure 8B:
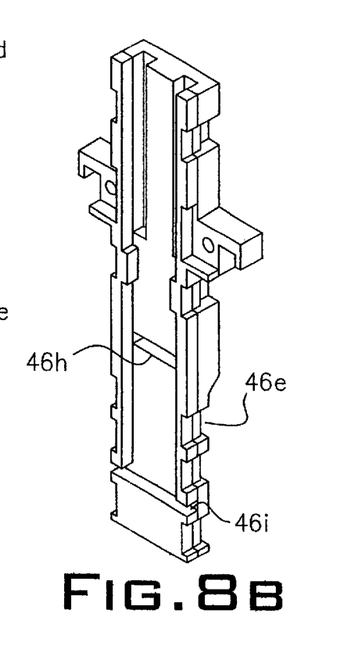
FIG. 8B is a perspective view of the inside of the back cover depicted in FIG. 8A.

An alternative design for the bias means that urges neck 44 of each cartridge toward the seed discharge chamber is depicted in FIG. 6. This alternate cartridge 40a has a flat handle 42 and a pair of transversely opposed, longitudinally extending, flexible and resilient plastic bias members 52a, 54a having a serpentine or sinusoidal configuration. The respective trailing ends of said bias members 52a, 54a are integrally formed with handle 42. The radially innermost end of each bias member is secured to or integrally formed with hollow housing 46 at connection points 46a, 46b so that the radially outermost (trailing) ends of said bias members urge neck 44 toward the seed discharge chamber. This design obviates the need for coil springs 52, 54 as the bias means but this design is more difficult to manufacture than the spring-based embodiment. Both designs represent an improvement over the earlier, loop-shaped bias means because the new designs substantially increase the number of seeds that a physician may implant without awkward replacement of the dispensing cartridge, and provide some shielding capability over the earlier designs.

Still further equivalent bias means are also within the scope of this invention. Obviously, springs 52, 54 need not be made of stainless steel but may be formed of any suitable material. Nor must bias members 52a, 54a be formed of plastic.

FIGS. 7A, 7B, 8A, and 8B provide structural details of hollow housing 46 (FIG. 4); note the two part structure. Each half part 46c, 46d has contiguous lands 46e or fingers 46f for snap-fit engagement with corresponding contiguous fingers and lands of its counterpart. The raised elements collectively denoted 46g are finger grips. Element 46h is an opening for loading seeds into housing 46 since neck 44 can be displaced upwardly, exposing this loading entrance opening. Element 46i is the seed discharge chamber formed within housing 46d thus precluding flash or irregularities in this most important seed transition area.

Housing 46 may be formed of a clear plastic so that the physician can see inside the housing and count the number of seeds therewithin. However, if the physician prefers to work with a shielded housing, such is also provided and is within the scope of this invention. In any event, neck 44 is marked with symbols 45a representing seeds as depicted in FIGS. 4 and 5. As neck 44 moves inwardly toward the elongate barrel with each discharge of a seed 45 from the seed discharge chamber, seed symbols 45a withdraw into housing 46 and the number of seed symbols remaining visible to inspection represents the number of seeds remaining within cartridge 40.

Those having expertise in the art of plastics molding will appreciate that the design disclosed herein is free of flashing and other imperfections of the type that could cause a seed to become lodged or jammed within hollow housing 46. They will also appreciate how the housing simply snaps together. This novel design overcomes the drawbacks of all heretofore known seed applicators by increasing their seed-holding capacity to sixteen seeds. Moreover, this novel design is non-jamming, provides significant shielding capabilities and therefore represents an important breakthrough in the art.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An interstitial brachytherapy device, comprising:
    an applicator;
    said applicator including an elongate barrel having a trailing end and a leading end;
    an adaptor mounted to said leading end of said elongate barrel, said adaptor enabling connection of a needle in leading relation to said elongate barrel;

an elongate throughbore formed in said elongate barrel, said elongate throughbore extending from said trailing end of said elongate barrel to said adaptor so that said elongate throughbore is in open communication with a lumen of said needle;

a manually-operated, elongate plunger rod adapted to be slidingly introduced into said elongate throughbore from a trailing end thereof;

a plurality of cartridge storage slots formed in said elongate barrel, said cartridge storage slots being longitudinally spaced apart from one another;

a plurality of cartridges adapted to be releasably coupled to said elongate barrel, each of said cartridges having a handle, an elongate neck integral with said handle, a hollow housing adapted to contain a plurality of radioactive seeds vertically stacked therewithin, a seed discharge chamber formed in a leading end of said housing, a biasing means that interconnects said housing and said handle and that urges a leading end of said neck to bear against a trailing radioactive seed in said stack of radioactive seeds, thereby urging a leading radioactive seed into said seed discharge chamber;

each of said cartridge storage slots being formed in said elongate barrel in non-intersecting relation to said elongate throughbore;

an operational slot formed in said elongate barrel near said leading end thereof;

said operational slot adapted to receive a preselected cartridge therein;

said seed discharge chamber of said preselected cartridge being in intersecting relation with said elongate throughbore when said preselected cartridge is positioned within said operational slot;

whereby a seed is discharged from said seed discharge chamber and introduced into said lumen of said needle when said elongate plunger rod is advanced from said trailing end to said leading end of said elongate throughbore;

whereby when all radioactive seeds have been discharged from said preselected cartridge, a second preselected cartridge is selected from said plurality of cartridges in said cartridge storage slots and introduced into said operational slot so that its seed discharge chamber is disposed in intersecting relation with said elongate throughbore.

2. The device of claim 1, wherein said biasing means is a pair of coil springs having respective trailing ends releasably secured to opposite sides of said handle and having respective leading ends releasably secured to opposite sides of said hollow housing.

3. The device of claim 1, wherein said biasing means is a pair of flexible and resilient plastic members of sinusoidal construction, each of said plastic members having a first end integrally formed with said handle and having a second end integrally formed with said hollow housing.

4. The device of claim 1, wherein said handle has a flat, circular area suitable for mounting a label thereon.

5. The device of claim 1, wherein said applicator is made of a clear plastic that enables visual inspection of its internal parts.

6. The device of claim 1, wherein said applicator is made of a material that shields against radiation exposure for any seeds positioned within the applicator body.

7. The device of claim 1, wherein said applicator is made of a material that maintains its functionality through repeated autoclave sterilization cycles, and wherein said applicator is easily disassembled for internal cleaning and part replacement.

8. An applicator that forms a part of an interstitial brachytherapy device, comprising:

an elongate barrel having a longitudinal axis of symmetry;

an elongate throughbore formed in said barrel, said elongate throughbore adapted to receive a radioactive seed;

a hollow needle mounted to a leading end of said elongate barrel;

a plurality of cartridge storage slots formed in said elongate barrel along its longitudinal extent;

each cartridge storage slot of said plurality of cartridge storage slots adapted to receive a radioactive seed-carrying cartridge therewithin;

said cartridge storage slots and said elongate throughbore being disposed in non-intersecting relation to one another so that a radioactive seed stored within a cartridge that is positioned within a cartridge storage slot can not enter into said throughbore;

an operational slot formed in said elongate barrel, said operational slot adapted to receive a cartridge that contains a plurality of seeds;

a seed discharge chamber formed in each of said cartridges;

a seed discharge chamber being in axial alignment with said elongate throughbore when a cartridge is positioned within said operational slot;

a connecting tube adapted to connect a seed discharge chamber to a needle lumen to preclude jamming as a seed transitions from said seed discharge chamber to the needle lumen;

said elongate throughbore bore adapted to slidingly receive a plunger rod that is adapted to push a seed in a seed discharge chamber out of said seed discharge chamber into said connecting tube and into said lumen of said needle.

9. The applicator of claim 8, further comprising a transversely disposed flat handle secured to a trailing end of said elongate barrel, said handle being apertured to receive said elongate plunger rod and said handle, elongate barrel, and needle collectively providing a syringe-like appearance.

10. A cartridge that forms a part of an interstitial brachytherapy device, comprising:

a hollow housing having a generally parallelepiped construction;

said hollow housing having a vertical extent substantially exceeding its respective width and depth extents;

said hollow housing adapted to receive a plurality of radioactive seeds that are vertically stacked within said hollow housing;

a handle having an elongate neck depending therefrom, said neck adapted to be slidingly received within said hollow housing;

said neck having a leading end that abuts an uppermost seed of said plurality of radioactive seeds;

a seed discharge chamber formed in said hollow housing at a lowermost end thereof;

a biasing means for urging said neck and hence said seeds toward said seed discharge chamber; and said biasing means having a first end secured to said hollow housing and a second end secured to said handle.

11. The cartridge of claim 10, wherein said handle includes a flat area that provides a mounting location for a label.

12. The cartridge of claim 10, wherein said handle is formed of a preselected material that provides at least some radiation shielding.

13. The cartridge of claim 10, wherein said housing has a front part made of transparent plastic so that the number of said radioactive seeds within said housing is ascertainable upon visual inspection of said housing.

14. The cartridge of claim 10, wherein said housing is opaque and shields against radiation.

15. The cartridge of claim 10, where a front part of said housing is made of transparent plastic and a back part of said housing is formed of an opaque material that shields against radiation.

16. The cartridge of claim 10, wherein a plurality of vertically spaced apart symbols are provided along the extent of said neck so that when said neck is disposed within said hollow housing the number of visible symbols on said neck represents the number of radioactive seeds within said housing.

17. A method for implanting radioactive seeds in a prostate gland or other internal organ, comprising the steps of:

providing a plurality of cartridges where each cartridge includes a hollow housing for receiving a plurality of radioactive seeds that are stacked relative to one another within said hollow housing;

providing a seed discharge chamber at a leading end of each hollow housing;

providing each cartridge with a handle and a neck formed integrally with said handle;

adapting said neck to be slideably received within said housing so that a leading end of said neck abuts against an uppermost seed in said stack of radioactive seeds;

biasing said neck to urge against said uppermost seed and hence against all seeds in said stack, driving a lowermost seed into said seed discharge chamber and driving a next lowermost seed into said seed discharge chamber when said lowermost seed is discharged from said discharge chamber;

providing an elongate applicator having an elongate throughbore formed therein;

mounting a hollow needle at a leading end of said applicator so that a lumen of said needle is in open communication and axial alignment with said elongate throughbore;

forming a plurality of cartridge storage slots in said applicator along its longitudinal extent so that said cartridge storage slots are longitudinally spaced apart from one another and so that said cartridge storage slots are in non-intersecting relation to said elongate throughbore;

forming an operational slot in said applicator near a leading end thereof, said operational slot intersecting said elongate throughbore, and adapting said operational slot to receive a leading end of a hollow housing of a preselected cartridge such that a seed discharge chamber is in axial alignment with said elongate throughbore;

inserting a cartridge into each of said cartridge storage slots by inserting a leading end of a hollow housing of a cartridge into a preselected cartridge storage slot;

inserting a plunger rod into said elongate throughbore and driving a seed in said seed discharge chamber into a prostate gland or other internal organ through a lumen of said hollow needle and repeatedly using said plunger rod until all seeds contained within said first cartridge are driven from said seed discharge chamber; and removing a second cartridge from one of said cartridge slots and inserting a leading end of a hollow housing of said second cartridge into said operational slot and repeatedly inserting said plunger rod until all seeds contained within said second cartridge are driven from said seed discharge chamber; and repeating said previous step with additional cartridges retrieved from said cartridge storage slots.

* * * * *